(12) United States Patent  (10) Patent No.: US 8,539,690 B2
Haykeen  (45) Date of Patent: Sep. 24, 2013

(54) WALL MOUNTABLE HEIGHT MEASURING DEVICE

(76) Inventor: Zohar Haykeen, Valley Village, CA (US)

( * ) Notice: Subject to any disclaimer, the term of this patent is extended or adjusted under 35 U.S.C. 154(b) by 203 days.

(21) Appl. No.: 13/274,795

(22) Filed: Oct. 17, 2011

(65) Prior Publication Data
US 2013/0091718 A1  Apr. 18, 2013

(51) Int. Cl.
*A61B 5/103* (2006.01)
(52) U.S. Cl.
USPC .......................................... 33/512; 600/587
(58) Field of Classification Search
USPC .................... 33/486, 487, 488, 512
See application file for complete search history.

(56) References Cited

U.S. PATENT DOCUMENTS

| 1,974,085 | A | * | 9/1934 | Shields et al. | 33/512 |
| 2,386,181 | A | * | 10/1945 | Bailey | 33/512 |
| 5,402,585 | A | * | 4/1995 | Lund | 33/832 |
| 6,073,359 | A | * | 6/2000 | Lee | 33/759 |
| 2010/0229412 | A1 | * | 9/2010 | Kenney | 33/512 |
| 2012/0096726 | A1 | * | 4/2012 | Glock, Jr. | 33/512 |
| 2012/0144686 | A1 | * | 6/2012 | Haykeen | 33/512 |

* cited by examiner

*Primary Examiner* — G. Bradley Bennett
(74) *Attorney, Agent, or Firm* — Thomas I. Rozsa

(57) ABSTRACT

A wall mountable height measuring device to record development of height of a person comprises a board, a pair of vertical slits, at least one linear measurement scale, a horizontal frame and a leveling bar. The board includes a front surface, a rear surface, a left side and a right side. The pair of vertical slits is present at the left side and right side of the board. The horizontal frame can slide along the pair of slits. A middle portion of the horizontal frame includes a cut out. A housing present at the middle portion of the leveling bar is for holding the at least one date stamp. The at least one date stamp indicates the date at which the height measurement was taken.

14 Claims, 4 Drawing Sheets

WALL MOUNTABLE HEIGHT MEASURING DEVICE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to height measuring devices, and more particularly to a wall mountable height measuring device for measuring and recording the changing height of a growing person.

DISCUSSION OF RELATED ART

Height is an important measurement for assessing the fitness of a person. A number of traditional height measuring devices have been developed in the art. These devices help the person to record progressive increases in height. Most conventional height measuring systems adopt a method in which, a person stands against a wall and the person's height is marked on the wall. Such markings will fade over time and become lost.

U.S. Pat. No. 7,059,060 issued to Baumgartner describes a device for recording both chronological events and physical growth events of an individual or group of individuals. The device includes a linear measuring device having at least first and second opposed sides. The first side has a linear measurement scale inscribed thereon and at least one recording surface associated therewith. The second side has a chronological scale, preferably in months and years, inscribed thereon and also has at least one recording surface associated with the chronological scale. Thus, physical growth can be measured on the first side and recorded on the recording surface associated therewith as the individual or several individuals grow. Significant events such as the date of height measurement can be recorded on the other side. However, this device has two separate sides for measuring height and date and both measurements cannot be recorded simultaneously. Further, the device is not wall mountable.

U.S. Pat. No. 6,226,881 issued to Landauer describes a height-measuring device that is foldable, or collapsible, on itself, in order to provide an easier and less-costly method of packaging and shipping. The height measuring device consists of an extensible leg or setup section that is mounted in the rear of the scale-part. The extensible leg has a length equal to the lowest measurement reading of the scale-section. The bottom edge surface of the scale-part can be readily located during installation of the height measuring device. However, the device has no arrangement to record the date at which the height measurement was taken.

U.S. Pat. No. 4,196,521 issued to Hutchinson describes a height measuring device that includes telescopically arranged measuring rods with faces containing parallel vertical columns of different types of height measuring units such as English measuring units and metric measuring units. However, this height measuring device is quite heavy and hence not portable.

Therefore, there is a need for an improved height measuring device that would accurately measure the changing height of a growing person. Such a needed device would have an arrangement to simultaneously record the height and date at which the measurement was taken. Further, such a device would be portable and wall mountable. The present invention accomplishes these objectives.

SUMMARY OF THE INVENTION

The present invention is a wall mountable height measuring device to record development of height of a person. The wall mountable height measuring device comprises a board, a pair of vertical slits, at least one linear measurement scale, a horizontal frame and a leveling bar. The horizontal frame can be slide along the pair of vertical slits of the board and includes a cut out at a middle portion of the horizontal frame. The horizontal frame may be made of plastic or the like. The board includes a front surface, a rear surface, a left side and a right side. One of the pair of vertical slits is formed on the left side and other one of the pair of vertical slits is formed on the right side. A cut out is present at a middle portion of the horizontal frame to mark the date. A housing present on the leveling bar is adaptable to hold at least one date stamp. The at least one date stamp indicates the date at which the height measurement was taken. The leveling bar may be attached at a middle portion of the horizontal frame and is utilized to slide along the pair of vertical slits to place over head of a person. The wall mountable height measuring device may be mounted on a wall by means of at least one attachment means.

The present invention facilitates an efficient way for accurately measuring the changing height of a growing person. Such a device has an arrangement to simultaneously record the height and date at which the measurement was taken. Further, such a device is portable and wall mountable. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Figure 1:
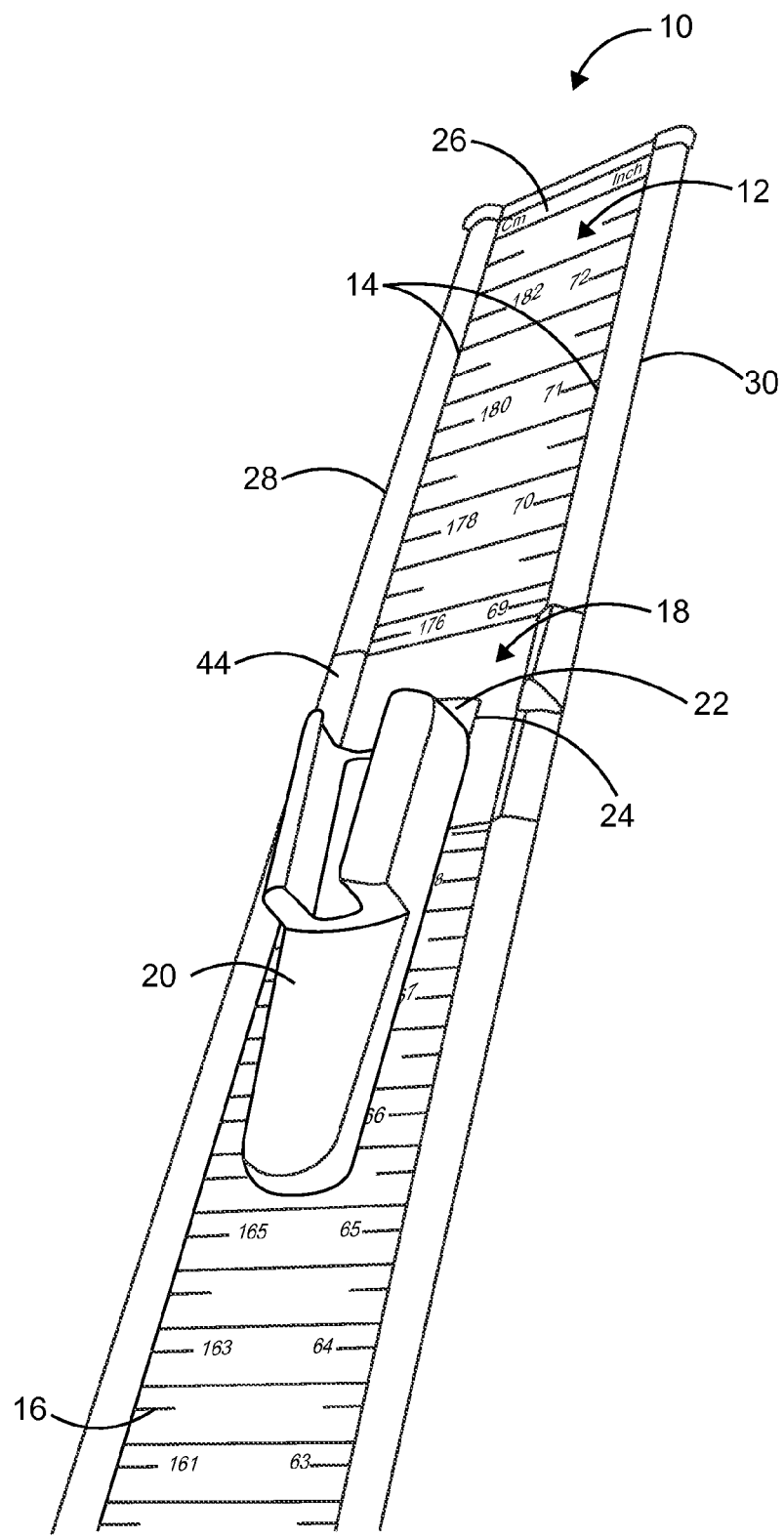
FIG. 1 is a perspective view of the present invention, illustrating a wall mountable height measuring device.

FIG. 1 is a perspective view of a wall mountable height measuring device 10 to record development of height of a person (not shown). The wall mountable height measuring device 10 comprises a board 12, a pair of vertical slits 14, at least one linear measurement scale 16, a horizontal frame 18 and a leveling bar 20. The horizontal frame 18 can slide along the pair of vertical slits 14. A cut out 22 is present at a middle portion 24 of the horizontal frame 18. The board 12 includes a front surface 26, a rear surface (not shown), a left side 28 and a right side 30. One of the pair of vertical slits 14 are formed on the left side 28 and other one of the pair of vertical slits 14 are formed on the right side 30. The cut out 22 is adaptable to hold at least one date stamp (not shown). The at least one date stamp (not shown) indicates the date at which the height measurement was taken. The leveling bar 20 may be attached at the middle portion 24 of the horizontal frame 18 and may be adaptable to place over head of a person (not shown). The wall mountable height measuring device 10 is portable. The wall mountable height measuring device 10 may be mounted on a wall by means of at least one attachment means (not shown). The at least one attachment means (not shown) may be selected from a group consisting of screws, bolts, clamps, and two sided tape. A pair of locking means 38 is then employed to lock the at least one linear measurement scale 16 on to the board 12.

Figure 2:
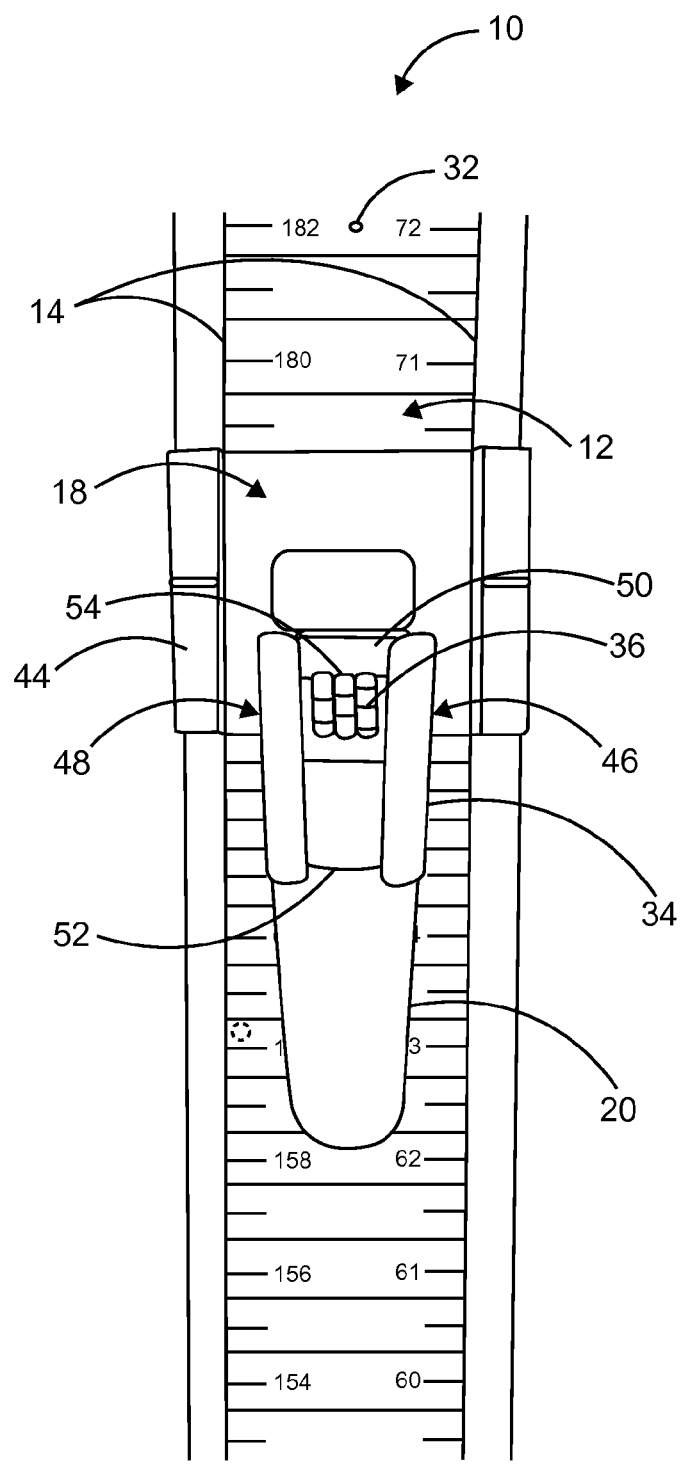
FIG. 2 is a front side view of the present invention, illustrating a horizontal frame.

FIG. 2 is a front side view of the wall mountable height measuring device 10, illustrating the horizontal frame 18. The wall mountable height measuring device 10 may be attached to the wall by a plurality of attachment means 32. The plurality of attachment means 32 may be a plurality of screws or the like. The horizontal frame 18 may be attached to the board 12 by a sliding means 44 along the pair of vertical slits 14. The sliding means 44 conforms to the left side 28 and the right side 30 of the board 12 to allow vertical movement along the length of the board 12. The leveling bar 20 present on the horizontal frame 18 includes a housing 34 for holding the at least one date stamp 36. The date stamp 36 may be used to indicate the date of the measurement taken. The housing 34 is composed of at least two sides, a left side 46 and a right side 48 to contain and hold the date stamp 36. The housing 34 also has a front opening 50 and a back opening 52. The front opening 50 allows access for the user to push the date stamp 36 forward. The date stamp 36 includes a front portion 54 to allow the user to push the date stamp 36 such that the ink portion comes into contact with the at least one linear measurement scale 16.

Figure 3:
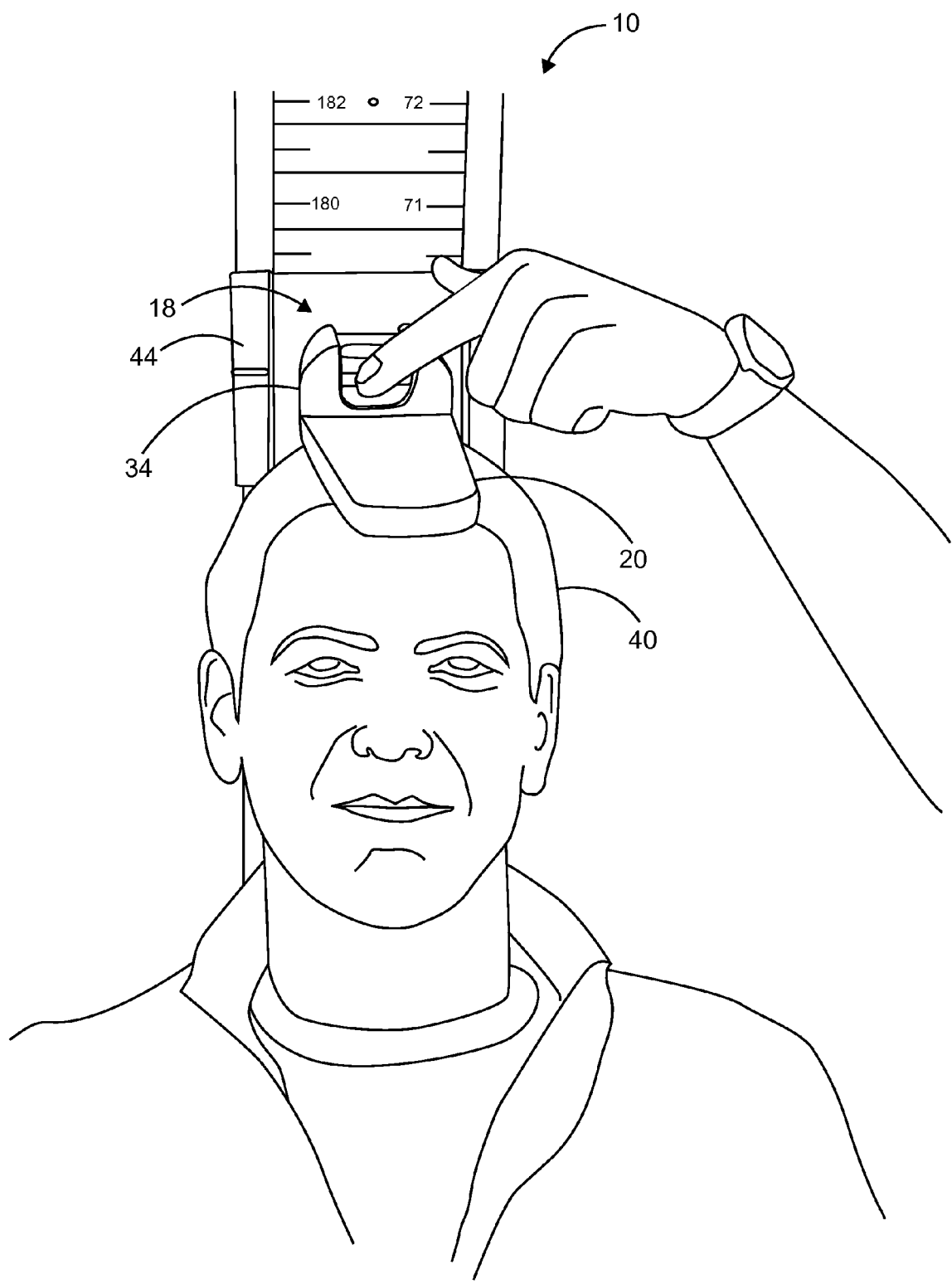
FIG. 3 is a front perspective view of the present invention, illustrating a leveling bar.

FIG. 3 is a front perspective view of the invention, illustrating the leveling bar 20. The leveling bar 20 is attached to the horizontal frame 18. The leveling bar 20 may extend by way of an attachment means (not shown) to the horizontal frame 18. The leveling bar 20 points in a downward direction relative to the ground when the device 10 is not in use. When in use, the leveling bar 20 is extendable such that it is placed over the head of the person 40. The housing 34 connected to the leveling bar 20 has a back portion (not shown) having a dimension which prevents the leveling bar 20 from extending over a 90 degree angle relative to the device 10. Consequently, keeping the leveling bar 20 at 90 degrees allows for a more accurate measurement.

Figure 4:
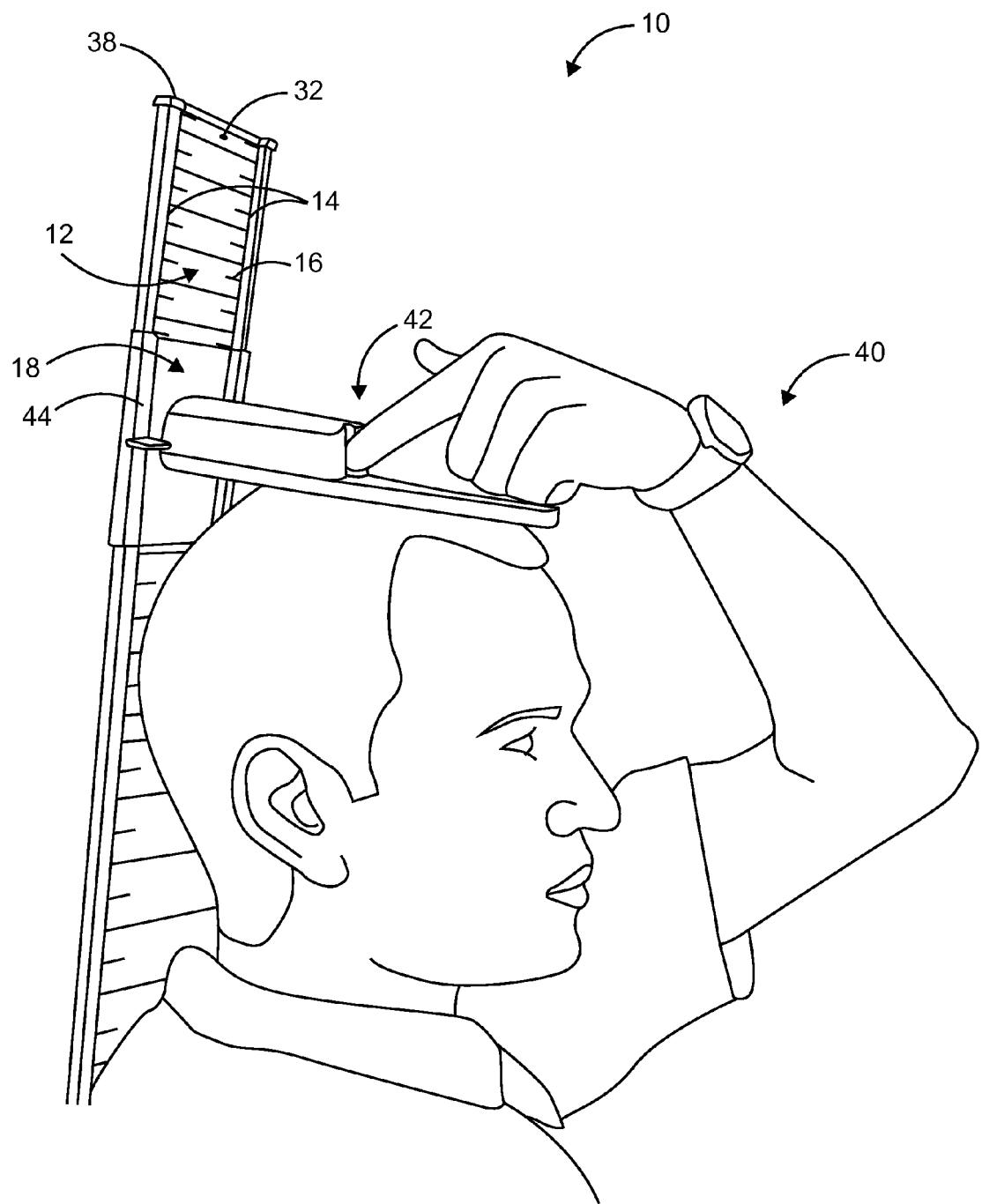
FIG. 4 is a perspective view of the present invention, illustrating the wall mountable height measuring device in use.

FIG. 4 is a perspective view of the invention, illustrating the wall mountable height measuring device 10 in use. While in use, the wall mountable height measuring device 10 is mounted on the wall by means of the at least one attachment means 32 and the person 40 is positioned against the board 12. The horizontal frame 18 can be slided along the pair of vertical slits 14 towards the head of the person 42. The leveling bar 20 is placed over the head of the person 42. The accurate measurement of the height is taken from the at least one linear measurement scale 16. The at least one date stamp 36 is inserted into the housing 34.

While a particular form of the invention has been illustrated and described, it will be apparent that various modifications can be made without departing from the spirit and scope of the invention. Accordingly, it is not intended that the invention be limited, except as by the appended claims.

What is claimed is:

1. A wall mountable height measuring device comprising:
    a board having a front surface, a rear surface, a left side and a right side;
    at least one linear measurement scale attached on the board;
    a horizontal frame having at least two sliding means;
    a cut out at a middle portion of the horizontal frame;
    a leveling bar attached to a middle portion of the horizontal frame; and
    a housing for holding at least one date stamp;
    whereby the housing is designed to hold at least one date stamp to record development of height of a person.

2. The wall mountable height measuring device of claim 1 wherein the leveling bar may be adaptable to place over head of the person.

3. The wall mountable height measuring device of claim 1 wherein a pair of vertical slits are formed on the left side and other one of the pair of slits formed on the right side.

4. The wall mountable height measuring device of claim 3 wherein the horizontal frame is adaptable to slide over the slits.

5. The wall mountable height measuring device of claim 1 wherein the sliding means of the horizontal frame conforms to the left side and the right side of the board to allow vertical movement of the horizontal frame along the board.

6. The wall mountable height measuring device of claim 1 wherein the at least one linear measurement scale is attached on to the board employing a pair of locking means.

7. The wall mountable height measuring device of claim 1 wherein the device may be mounted on a wall by means of at least one attachment means.

8. The wall mountable height measuring device of claim 1 wherein the at least one attachment means may be selected from a group consisting of: screws, bolts, clamps, and two sided tapes.

9. The wall mountable height measuring device of claim 1 wherein the at least one date stamp may be inserted into the housing.

10. The wall mountable height measuring device of claim 1 wherein the height measuring device is portable.

11. The wall mountable height measuring device of claim 1 wherein the at least one linear measurement scale may be utilized to measure the height in feet/inches and in centimeters.

12. A method for measuring and recording height of a person employing a wall mountable height measuring device, the method comprising the steps of:
    a) providing a wall mountable height measuring device;
    b) mounting the wall mountable height measuring device on a wall;
    c) positioning a person against a board associated to the height measuring device;
    d) sliding a horizontal frame along a pair of vertical slits towards head of the person;
    e) placing a leveling bar over the head of the person;
    f) taking an accurate measurement from at least one linear measurement scale on the board;
    g) inserting at least one date stamp into a housing present in the horizontal frame;
    h) pushing the date stamp towards the board to mark the measurement; and
    i) marking the date of the measurement taken.

13. The method of claim 12 wherein the at least one date stamp indicates the date at which the height measurement was taken.

14. The method of claim 12 wherein the wall mountable height measuring device may be mounted on a wall by means of at least one attachment means.

* * * * *